US011166740B1

(12) United States Patent
Schumaier et al.

(10) Patent No.: US 11,166,740 B1
(45) Date of Patent: Nov. 9, 2021

(54) ILLUMINATED TWEEZERS

(71) Applicant: Ear Technology Corporation, Johnson City, TN (US)

(72) Inventors: Daniel R. Schumaier, Elizabethton, TN (US); Karlee D. Harrison, Johnson City, TN (US); George B. Waites, Jr., Fletcher, NC (US); Samuel C. Scudder, Asheville, NC (US)

(73) Assignee: Ear Technology Corporation, Johnson City, TN (US)

( * ) Notice: Subject to any disclaimer, the term of this patent is extended or adjusted under 35 U.S.C. 154(b) by 0 days.

(21) Appl. No.: 17/213,305

(22) Filed: Mar. 26, 2021

(51) Int. Cl.
 *A61B 17/30* (2006.01)
 *A61B 90/35* (2016.01)
 *A61B 17/00* (2006.01)

(52) U.S. Cl.
 CPC .............. *A61B 17/30* (2013.01); *A61B 90/35* (2016.02); *A61B 2017/00734* (2013.01); *A61B 2017/00907* (2013.01); *A61B 2017/305* (2013.01)

(58) Field of Classification Search
 CPC ......... A61B 17/30; A61B 17/50; A61B 17/52; A61B 2017/305; A61B 2017/00902; A61B 2017/00907; A61B 2017/00734; A61B 2017/505; A61B 90/35; A61B 90/30
 USPC .................................................. 606/210–211
 See application file for complete search history.

(56) References Cited

U.S. PATENT DOCUMENTS

| | | | | |
|---|---|---|---|---|
| 2,885,537 | A | * | 5/1959 | Wood, Jr. ............... A61B 17/24 362/119 |
| 4,572,180 | A | | 2/1986 | Deenadayalu |
| 4,785,796 | A | | 11/1988 | Mattson |
| 5,209,757 | A | | 5/1993 | Krug et al. |
| 5,234,452 | A | | 8/1993 | Wang-On |
| 6,074,405 | A | | 6/2000 | Koch |
| 6,179,847 | B1 | * | 1/2001 | Possum .................. A61B 17/50 606/131 |
| 6,730,076 | B2 | | 5/2004 | Hickingbotham |
| 9,167,959 | B1 | * | 10/2015 | Rubtsov ................ A61B 1/313 |
| 10,092,168 | B1 | | 10/2018 | Huttner et al. |

(Continued)

FOREIGN PATENT DOCUMENTS

| CN | 2192310 | 3/1995 |
|---|---|---|
| CN | 2355698 | 12/1999 |
| CN | 201618004 U | 11/2010 |

(Continued)

*Primary Examiner* — Katherine H Schwiker
(74) *Attorney, Agent, or Firm* — Luedeka Neely Group, P.C.

(57) ABSTRACT

A tweezer assembly includes a housing, an optically-transmissive shaft, and a flexible arm. A lamp is disposed within the housing and adjacent the opening in the housing. A battery provides electrical power to the lamp. The shaft has external threads that match the internal threads of the opening in the housing. The flexible arm includes an arched section and a clamp disposed at its proximal end. The clamp has opposing jaws that flex outward to snap in place around opposing sides of a recessed section in the shaft. The clamp thereby secures the flexible arm to the shaft such that the distal end of the arched section is disposed proximate to but not contacting the distal end of shaft. When a pressing force is applied to the arched section, the distal end of the flexible arm is operable to move into contact with the distal end of the shaft.

14 Claims, 4 Drawing Sheets

(56) References Cited

U.S. PATENT DOCUMENTS

2004/0181255 A1    9/2004  Gio

FOREIGN PATENT DOCUMENTS

| | | |
|---|---|---|
| CN | 201759742 U | 3/2011 |
| CN | 201959081 U | 9/2011 |
| CN | 203953746 U | 11/2014 |
| CN | 204016615 U | 12/2014 |
| CN | 205458567 U | 8/2016 |
| CN | 209075144 U | 7/2019 |
| CN | 210355086 U | 4/2020 |
| CN | 211934525 U | 11/2020 |

* cited by examiner

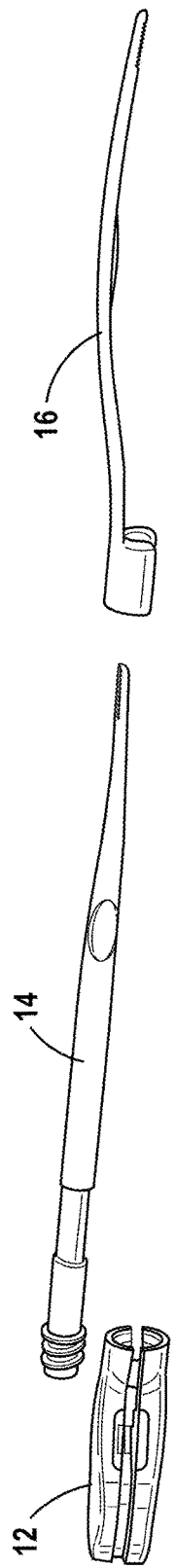
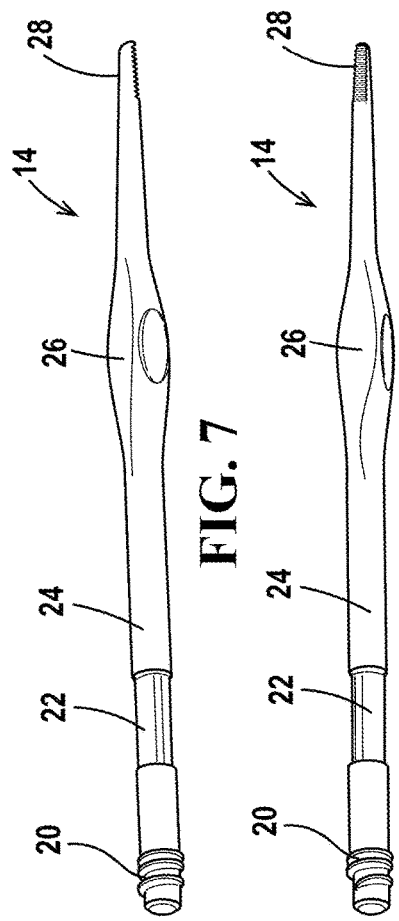
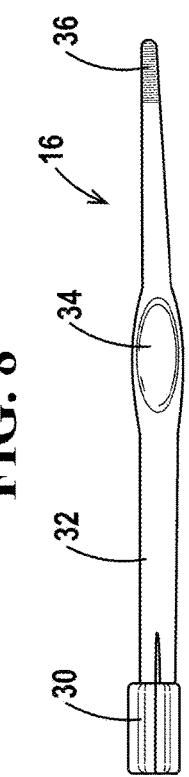
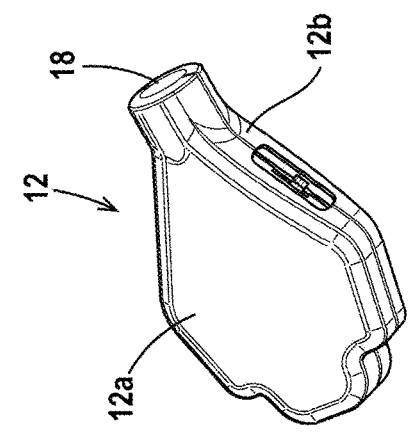
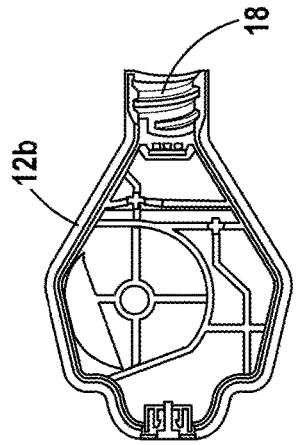

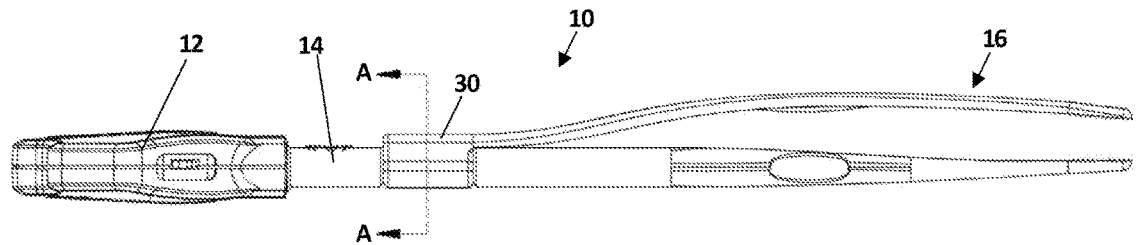
FIG. 11A
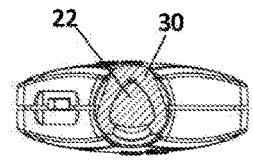
FIG. 11B
(Section A-A)
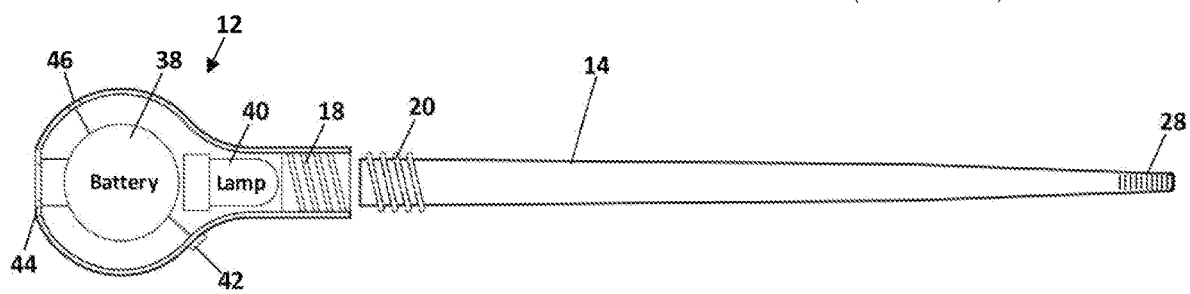
FIG. 12
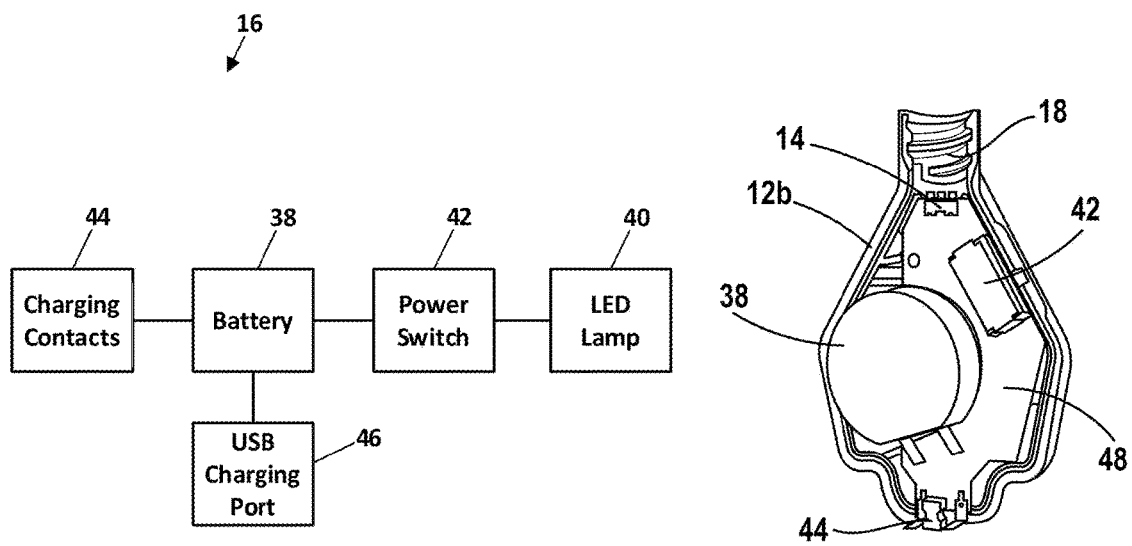
FIG. 13  FIG. 14

ILLUMINATED TWEEZERS

FIELD

This invention relates to the field of medical instruments. More particularly, this invention relates to illuminated tweezers for use in removing obstructions from the ear canal.

BACKGROUND

The buildup and impaction of cerumen in the outer ear canal can lead to hearing loss, irritation and pain in the ear, dizziness, ringing in the ears and other problems. A trained medical practitioner, such as a physician or audiologist, typically uses a curette to scrape and remove cerumen from the ear canal. Although this is a straightforward process, the lack of sufficient light can make the procedure much more difficult.

Lighted curettes are available that provide illumination to the ear canal during a cerumen removal procedure. However, none of the known lighted curette instruments provide means for scraping and then grasping loose cerumen for removal.

Although, it is known to attach a light source to tweezers, the available lighted tweezer devices are flimsy and generally do not provide efficient light transmission to sufficiently illuminate the ear canal. Also, none of known lighted tweezers allow for removal of one arm of the tweezers so that the other arm can be used as a curette for scraping.

What is needed, therefore, is a sturdy illuminated tweezer instrument having improved light transmission and a removable arm so that the instrument can be used as a curette.

SUMMARY

The above and other needs are met by an illuminated tweezer assembly comprising a housing, an optically-transmissive elongate shaft, and a flexible arm. The housing has an opening with internal threads. A lamp is disposed within the housing and adjacent the opening. A battery is also disposed within the housing for providing electrical power to the lamp.

The elongate shaft includes a shaft portion having a proximal end and a distal end. Adjacent the proximal end of the shaft portion are external threads that match the internal threads of the opening in the housing. The shaft portion includes a recessed section disposed between its proximal and distal ends.

The flexible arm includes an arched central section having a proximal end and a distal end. A clamp structure is disposed at the proximal end of the arched central section. The clamp structure has opposing jaws that are operable to flex outward to snap in place around opposing sides of the recessed section of the elongate shaft. The clamp structure thereby secures the flexible arm to the elongate shaft such that the distal end of the arched central section is disposed proximate to but not contacting the distal end of the shaft of the elongate shaft. When a pressing force is applied to the arched central section of the flexible arm, the distal end of the arched central section is operable to move into contact with the distal end of the shaft of the elongate shaft.

In some embodiments, the opposing jaws of the clamp structure engage with opposing sides of the recessed section to prevent axial rotation of the flexible arm with respect to the elongate shaft.

In some embodiments, the cross-section of the clamp structure defines a curvilinear triangle on its inside surface, and the cross-section of the recessed section defines a curvilinear triangle on its outside surface that matches that of the clamp structure.

In some embodiments, a power switch is disposed within the housing for controlling electrical power to the lamp.

In some embodiments, the elongate shaft is molded from optically transmissive polycarbonate.

In some embodiments, the elongate shaft includes a grip disposed between the recessed section and the distal end of the shaft.

In some embodiments, the flexible arm includes a finger pad disposed on the arched central section between the clamp structure and the distal end of the arched central section.

In some embodiments, a tip is disposed at the distal end of the elongate shaft and a tip is disposed at the distal end of the flexible arm. Each tip includes a face that opposes a face on the other tip, and each face includes molded rib features to provide an enhanced grip on objects grabbed between the opposing faces.

In some embodiments, charging means are disposed on the housing for charging the battery, such as a USB charging port and/or a pair of charging contacts.

In some embodiments, when the external threads of the elongate shaft are fully engaged with the internal threads of the housing, the elongate shaft is operable to propagate light from the lamp along the length of the shaft to illuminate at least the distal end of the shaft.

In some embodiments, the lamp comprises a light emitting diode (LED).

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 4 depicts an exploded view of the lighted tweezers assembly according to an embodiment of the invention;

FIG. 5 depicts an electronics housing of the lighted tweezers assembly according to an embodiment of the invention;

FIG. 6 depicts a cutaway view of the electronics housing of the lighted tweezers assembly according to an embodiment of the invention;

FIGS. 7 and 8 depict an elongate shaft of the lighted tweezers assembly according to an embodiment of the invention;

FIGS. 9 and 10 depict a flexible arm of the lighted tweezers assembly according to an embodiment of the invention;

FIG. 11A depicts an elevation view of the lighted tweezers assembly according to an embodiment of the invention;

FIG. 11B depicts a cross-section view of the lighted tweezers assembly according to an embodiment of the invention;

FIG. 12 depicts a simplified view of internal components of the electronics housing, with the elongate shaft removed from the housing according to an embodiment of the invention;

FIG. 13 depicts a schematic electrical diagram of the lighted tweezers assembly according to an embodiment of the invention;

FIG. 14 depicts the layout of the internal components of the electronics housing of the lighted tweezers assembly according to an embodiment of the invention.

DETAILED DESCRIPTION

Figure 1:
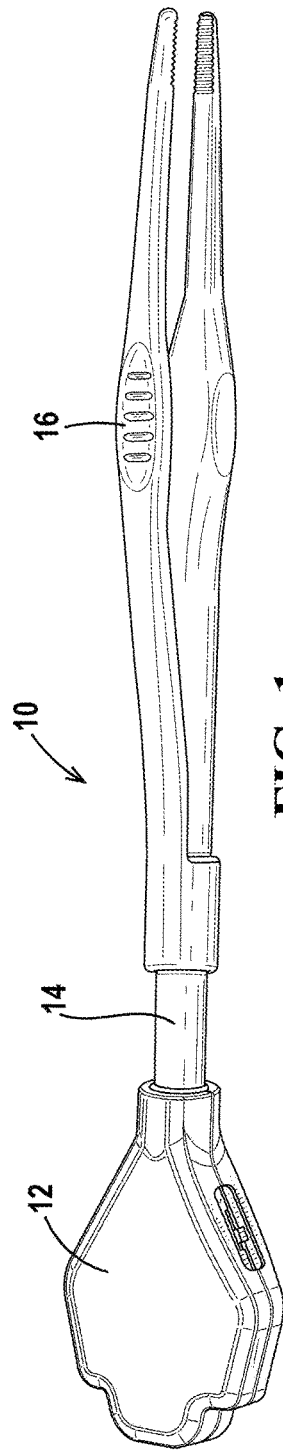
FIGS. 1-3 depict a lighted tweezers assembly according to an embodiment of the invention.
Figure 2:
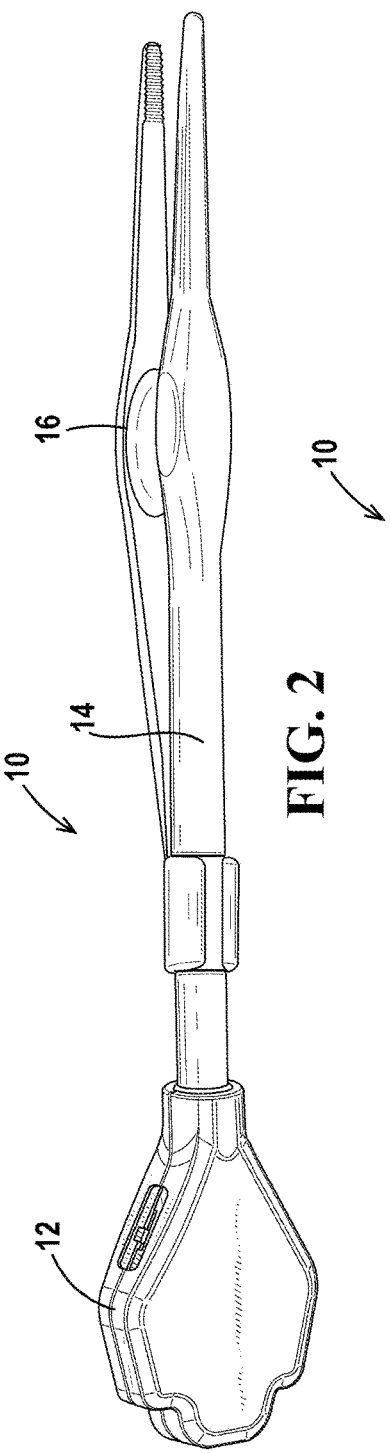
Figure 3:
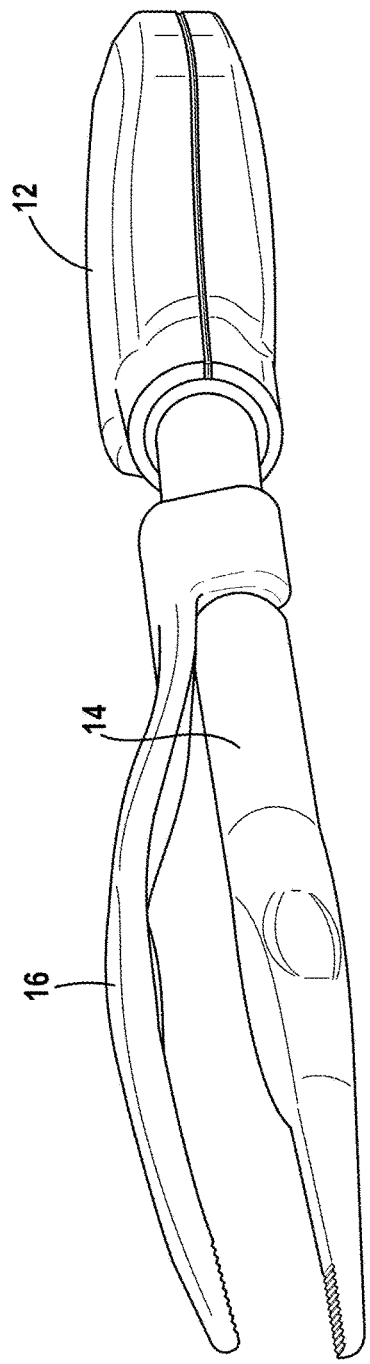

As depicted in FIGS. 1-4, a preferred embodiment of a lighted tweezers assembly 10 includes an electronics housing 12, a light-transmissive elongate shaft 14, and a flexible arm 16. As shown in FIGS. 12 and 13, a battery 38 disposed within the housing 12 provides power for a lamp 40, such as a light-emitting diode (LED). A power switch 42 is provided on the housing 12 to control the on/off state of the lamp 40. The battery 38 may be charged via a pair of charging contacts 44 or via a USB charging port 46. Within the end of the housing 12 is a threaded aperture 18 having internal threads that match external threads 20 on an end of the elongate shaft 14. In a preferred embodiment, the elongate shaft 14 is molded from optically-clear polycarbonate that conducts light from the lamp 40 down the length of the elongate shaft 14.

Figure 15A:
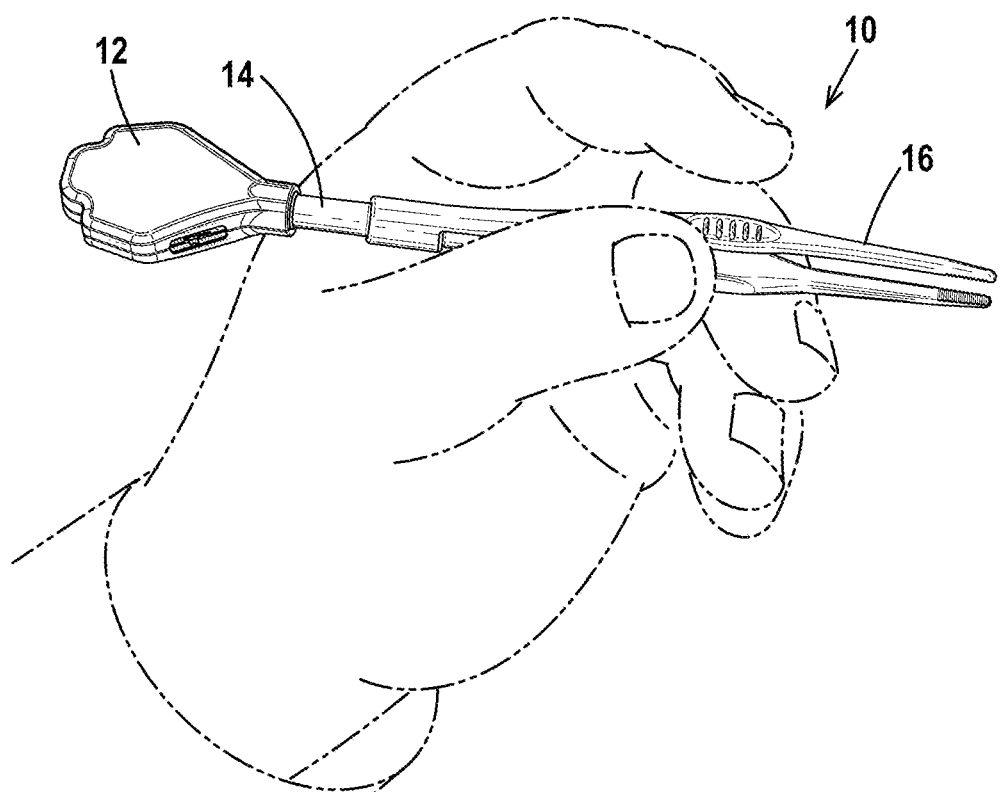
FIGS. 15A-15B depict a user holding and operating an embodiment of the lighted tweezers assembly.
Figure 15B:
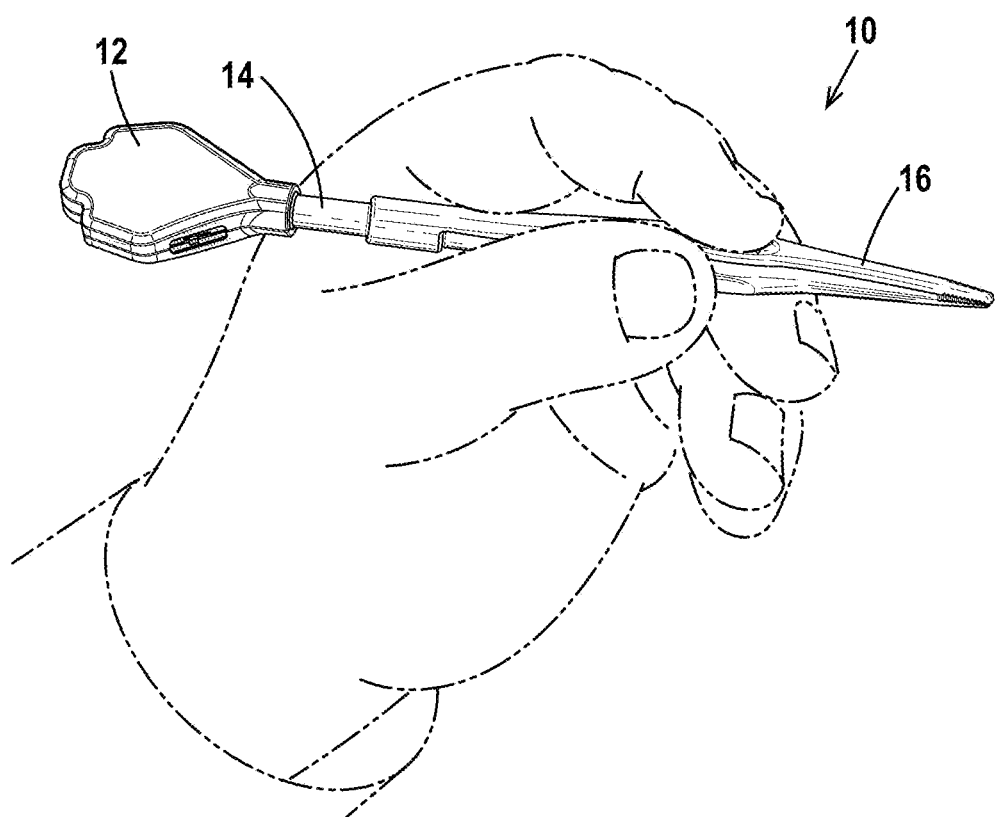

As shown in FIGS. 7 and 8, the elongate shaft 14 includes a cylindrical shaft portion 24 having a length of about 5.5 inches and a diameter of about 0.25 inch, with the threads 20 disposed at its proximal end and a tip 28 disposed at its distal end. A grip 26, which is centrally disposed on the shaft portion 24, includes pads on opposing sides at which the grip 26 is held between the user's thumb and middle finger, as shown in FIGS. 15A-15B. In a preferred embodiment, a recessed section 22 of the elongate shaft 14 has a cross-section shaped as a curvilinear triangle.

As shown in FIGS. 9 and 10, the flexible arm 16 comprises an arched central section 32 having a clamp section 30 disposed at its proximal end and a tip 36 disposed at its distal end. A finger pad 34 is centrally disposed on the central section 32 upon which the index finger of the user presses when in use, as shown in FIGS. 15A-15B. As shown in the cross-section view of FIG. 11B, the clamp section 30 has opposing jaws that can flex outward and snap around the recessed section 22 of the elongate shaft 14. The matching curvilinear triangular shape of the outer surface of the recessed section 22 and the inner surface of the clamp section 30 prevents rotation of the flexible arm 16 relative to the elongate shaft 14. In a preferred embodiment, the flexible arm 16 is also molded from polycarbonate, although there is no need for it to be optically clear.

The opposing faces of the tips 28 and 36 of the elongate shaft 14 and the flexible arm 16 preferably include molded rib features to provide an enhanced grip on objects grabbed therebetween.

FIG. 14 depicts the electrical components within the housing 12, wherein the housing portion 12a is removed to reveal a preferred layout of the components on a printed circuit board 48. The housing portions 12a and 12b are preferably molded from polycarbonate.

It will be appreciated that the ability to easily detach the tweezer portions 14 and 16 from the housing 12 allows for the use of disposable low-cost tweezer portions, while keeping the housing portion—with its higher-cost electronic components—available for multiple uses. Other advantages of the embodiments described herein include:

Threaded shaft interface. The threaded connection of the elongate shaft to the housing prevents the elongate shaft from popping out of the housing during use.

Improved light transmission. The elongate shaft is substantially straight, and has sufficient diameter to provide for efficient light transmission down its length. A bent shaft, such as is found in prior lighted tweezers, does not provide efficient light transmission, because the bent shaft results more loss of light as it travels down the shaft.

Curette and tweezer in one instrument. The flexible arm can be removed from the shaft so that the shaft portion alone can be used as a curette for scraping.

Durable shaft. The large diameter and straightness of the elongate shaft provides for improved durability.

Easier to control. The use of a straight sturdy shaft combined with an arched flexible arm results in an instrument that has enhanced dexterity control. It is easier to hold and manipulate as compared to known tweezer instruments.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An illuminated tweezer assembly comprising:
 a housing having an opening with internal threads;
 a lamp disposed within the housing and adjacent the opening;
 a battery disposed within the housing for providing electrical power to the lamp;
 an elongate shaft that is optically-transmissive, the elongate shaft comprising:
  a shaft portion having a proximal end and a distal end;
  external threads disposed adjacent the proximal end of the shaft portion, the external threads matching the internal threads of the opening in the housing; and
  a recessed section disposed in the shaft portion between the proximal end and the distal end of the shaft portion; and
 a flexible arm comprising:
  an arched central section having a proximal end and a distal end; and
  a clamp structure disposed at the proximal end of the arched central section, the clamp structure having opposing jaws that are operable to flex outward to snap in place around opposing sides of the recessed section of the elongate shaft, thereby securing the flexible arm to the elongate shaft such that the distal end of the arched central section is disposed proximate to but not contacting the distal end of the shaft portion,
 wherein as a pressing force is applied to the arched central section of the flexible arm, the distal end of the arched central section is operable to move into contact with the distal end of the shaft portion.

2. The illuminated tweezer assembly of claim 1 wherein the opposing jaws of the clamp structure engage with the opposing sides of the recessed section to prevent axial rotation of the flexible arm with respect to the elongate shaft.

3. The illuminated tweezer assembly of claim 2 wherein a cross-section of the clamp structure defines a curvilinear triangle on an inside surface of the clamp structure, and a cross-section of the recessed section defines a curvilinear triangle on an outside surface of the recessed section that matches the curvilinear triangle of the clamp structure.

4. The illuminated tweezer assembly of claim 1 further comprising a power switch disposed within the housing for switching electrical power to the lamp on and off.

5. The illuminated tweezer assembly of claim 1 wherein the elongate shaft is molded from optically transmissive polycarbonate.

6. The illuminated tweezer assembly of claim 1 wherein the elongate shaft further comprises a grip disposed on the shaft portion between the recessed section and the distal end of the shaft portion.

7. The illuminated tweezer assembly of claim 1 wherein the flexible arm further comprises a finger pad disposed on the arched central section between the clamp structure and the distal end of the arched central section.

8. The illuminated tweezer assembly of claim 1 wherein a tip is disposed at the distal end of the shaft portion and a tip is disposed at the distal end of the arched central section, wherein each tip includes a face that opposes a face on the other tip, and wherein each face includes molded rib features to provide an enhanced grip on objects grabbed between the opposing faces.

9. The illuminated tweezer assembly of claim 1 further comprising charging means disposed on the housing for charging the battery.

10. The illuminated tweezer assembly of claim 9 wherein the charging means comprise one or both of a USB charging port and a pair of charging contacts.

11. The illuminated tweezer assembly of claim 1 wherein, when the external threads of the elongate shaft are fully engaged with the internal threads of the housing, the elongate shaft is operable to propagate light from the lamp along the length of the shaft portion to illuminate at least the distal end of the shaft portion.

12. The illuminated tweezer assembly of claim 1 wherein the lamp comprises a light emitting diode (LED).

13. The illuminated tweezer assembly of claim 1 wherein the elongate shaft is substantially straight.

14. An illuminated tweezer assembly comprising:
a housing having an opening with internal threads;
a lamp disposed within the housing and adjacent the opening;
a battery disposed within the housing for providing electrical power to the lamp;
a power switch disposed within the housing for switching electrical power to the lamp on and off;
an elongate shaft that is optically-transmissive, the elongate shaft comprising:
  a shaft portion having a proximal end and a distal end;
  external threads disposed adjacent the proximal end of the shaft portion, the external threads matching the internal threads of the opening in the housing, such that when the external threads of the elongate shaft are fully engaged with the internal threads of the housing, the elongate shaft is operable to propagate light from the lamp along the length of the shaft portion to illuminate at least the distal end of the shaft portion;
  a recessed section disposed in the shaft portion between the proximal end and the distal end of the shaft portion; and
  a grip disposed on the shaft portion between the recessed section and the distal end of the shaft portion; and
a flexible arm comprising:
  an arched central section having a proximal end and a distal end;
  a clamp structure disposed at the proximal end of the arched central section, the clamp structure having opposing jaws that are operable to flex outward to snap in place around opposing sides of the recessed section of the elongate shaft to prevent axial rotation of the flexible arm with respect to the elongate shaft, and thereby securing the flexible arm to the elongate shaft such that the distal end of the arched central section is disposed proximate to but not contacting the distal end of the shaft portion; and
  a finger pad disposed on the arched central section between the clamp structure and the distal end of the arched central section,
wherein as a pressing force is applied to the arched central section of the flexible arm, the distal end of the arched central section is operable to move into contact with the distal end of the shaft portion of the elongate shaft.

* * * * *